(12) United States Patent
Shapiro et al.

(10) Patent No.: US 7,547,787 B2
(45) Date of Patent: Jun. 16, 2009

(54) PROCESSES FOR PREPARING MONTELUKAST SODIUM

(75) Inventors: Evgeny Shapiro, Haifa (IL); Ronit Yahalomi, Kiryat Bialik (IL); Valerie Niddam-Hildesheim, Ein Vered (IL); Greta Sterimbaum, Rishon-Lezion (IL); Kobi Chen, Ramat HaSharon (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 625 days.

(21) Appl. No.: 11/112,790

(22) Filed: Apr. 21, 2005

(65) Prior Publication Data

US 2005/0256156 A1   Nov. 17, 2005

Related U.S. Application Data

(60) Provisional application No. 60/564,504, filed on Apr. 21, 2004, provisional application No. 60/582,237, filed on Jun. 22, 2004.

(51) Int. Cl.
*C07D 215/38* (2006.01)
(52) U.S. Cl. .................. 546/157; 546/153; 546/163
(58) Field of Classification Search ............... 546/153, 546/157, 163
See application file for complete search history.

(56) References Cited

U.S. PATENT DOCUMENTS

| | | | |
|---|---|---|---|
| 5,428,033 | A | 6/1995 | Belley et al. |
| 5,523,477 | A | 6/1996 | King et al. |
| 5,565,473 | A | 10/1996 | Belley et al. |
| 5,614,632 | A | 3/1997 | Bhupathy et al. |
| 5,750,539 | A | 5/1998 | Gareau et al. |
| 5,856,322 | A | 1/1999 | Belley et al. |
| 5,952,347 | A | 9/1999 | Arison et al. |
| 6,320,052 | B1 | 11/2001 | Bhupathy et al. |
| 6,333,198 | B1 | 12/2001 | Edmeades et al. |
| 6,716,452 | B1 * | 4/2004 | Piccariello et al. ........... 424/457 |
| 7,189,853 | B2 * | 3/2007 | Sundaram et al. ........... 546/180 |
| 2005/0107426 | A1 | 5/2005 | Overeem et al. |
| 2005/0107612 | A1 | 5/2005 | Reguri et al. |
| 2005/0187243 | A1 | 8/2005 | Niddam-Hildesheim et al. |
| 2005/0234241 | A1 | 10/2005 | Sundaram et al. |
| 2006/0004204 | A1 | 1/2006 | Reguri et al. |

FOREIGN PATENT DOCUMENTS

| | | |
|---|---|---|
| EP | 0 480 717 | 4/1992 |
| EP | 0 500 360 | 8/1992 |
| EP | 1 904 448 | 4/2008 |
| WO | WO 95/18107 | 7/1995 |
| WO | WO 99/65888 | 12/1999 |
| WO | WO 03/066598 | 8/2003 |
| WO | WO 2004/091618 | 10/2004 |
| WO | WO 2004/108679 | 12/2004 |
| WO | WO 2005/040123 | 5/2005 |
| WO | WO 2005/073194 | 8/2005 |
| WO | WO 2005/074893 | 8/2005 |
| WO | WO 2006/008751 | 1/2006 |
| WO | WO 2006/043846 | 4/2006 |
| WO | WO 2006/058545 | 6/2006 |

OTHER PUBLICATIONS

DuFresne,J Org Chem, VOl, pp. 8518-8525, 1996.*
King, et al., "An Efficient Synthesis Of LTD$_4$ Antagonist L-699,392", *J. Org. Chem.*, 1993, pp. 3731-3735, vol. 58, No. 14.
Labelle, et al., "Discovery Of MK-0476, A Potent And Orally Active Leukotriene D$_4$ Receptor Antagonist Devoid Of Peroxisomal Enzyme Induction", *Bioorg. Med. Lett.*, 1995, pp. 283-288, vol. 5, No. 3.
Snyder, et al., *Introduction To Modern Liquid Chromatography*, Second Ed., 1979, pp. 549, 552, 571-572.
Strobel, et al., *Chemical Instrumentation: A Systematic Approach*, Third Ed., 1989, pp. 391-393, 894, 922, 924-925, 953.
Office Action from related U.S. Appl. No. 11/048,283, mailed Feb. 7, 2008.
Office Action from related U.S. Appl. No. 11/048,276, mailed Feb. 20, 2008.
Office Action from related U.S. Appl. No. 11/601,113, mailed Oct. 22, 2007.
Third Party Observation filed for European Application No. 067863696.2101.
Dufresne et al., "Synthesis of Montelukast (MK-0476) Metabolic Oxidation Prodcuts", Journal of Organic Chemistry, (61) 8518-8525 (1996).
Guay et al., "A Series of Non-Quinoline $_{Cy5}$LT$_1$ Receptor Antagonist: SAR Study on Pyridyl Analogs of Singulair©" Biorganic & Medicinal Chemistry Letters, 8(5) 453-458 (1998).

* cited by examiner

Primary Examiner—D. Margaret Seaman
(74) *Attorney, Agent, or Firm*—Kenyon & Kenyon LLP

(57) ABSTRACT

The present invention provides processes for preparing montelukast.

27 Claims, 1 Drawing Sheet

PROCESSES FOR PREPARING MONTELUKAST SODIUM

This application claims the benefit of U.S. Provisional Patent Applications Ser. Nos. 60/564,504 filed Apr. 21, 2004 and 60/582,237 filed Jun. 22, 2004.

FIELD OF THE INVENTION

The present invention relates to processes for preparing montelukast sodium.

BACKGROUND OF THE INVENTION

Montelukast is a selective, orally active leukotriene receptor antagonist that inhibits the cysteinyl leukotriene $CysLT_1$ receptor. Leukotrienes are associated with the inflammation and constriction of airway muscles and the accumulation of fluid in the lungs. Montelukast sodium is a useful therapeutic agent for treating respiratory diseases such as asthma and allergic rhinitis.

The chemical name for montelukast sodium is: [R -(E)]-1-[[[1-[3-[2-(7-chloro-2-quinolinyl)ethenyl]phenyl]-3-[2-(1-hydroxy-1-methylethyl)phenyl]propyl]thio]methyl]cyclopropaneacetic acid, monosodium salt. Montelukast sodium salt is represented by the formula:

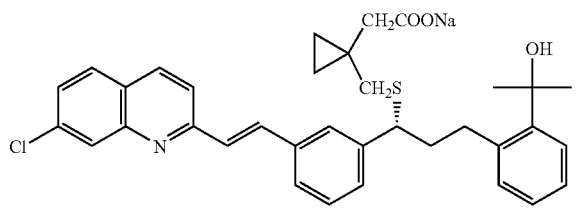

Montelukast sodium as marketed is a hygroscopic, optically active, white to off-white powder. Montelukast sodium is freely soluble in methanol, ethanol, and water and practically insoluble in acetonitrile.

U.S. Pat. No. 5,565,473 discloses a synthetic process for montelukast sodium, wherein the compound is obtained as an oil that is then dissolved in water and freeze-dried. The preparation method of the '473 patent is published at M. Labelle, et al. Bioorg. Med. Lett., 5 (3) 283-288 (1995). The synthesis method can be altered to allow for the preparation of montelukast related compounds. O. King, et al. J. Org. Chem., 58: 3731-3735 (1993).

U.S. Pat. No. 5,614,632 claims a method of synthesis where montelukast is obtained by the nucleophilic substitution of a chiral mesitylate group with the dilithium dianion of the 1-(mercaptomethyl) cyclopropaneacetic acid with simultaneous inversion of configuration. It is highly desirable to preserve the chirality of the product, that is, to avoid racemization. In the '632 patent the formation of the dilithium dianion is realized with butyl lithium. U.S. Pat. No. 5,523,477 claims an improved method for the preparation of 1-(mercaptomethyl) cyclopropaneacetic acid.

Because butyl lithium is a dangerous and expensive reagent, there is a need for other methods for preparing montelukast that utilize other reagents while preserving the chirality of the product.

SUMMARY OF THE INVENTION

Figure 1:
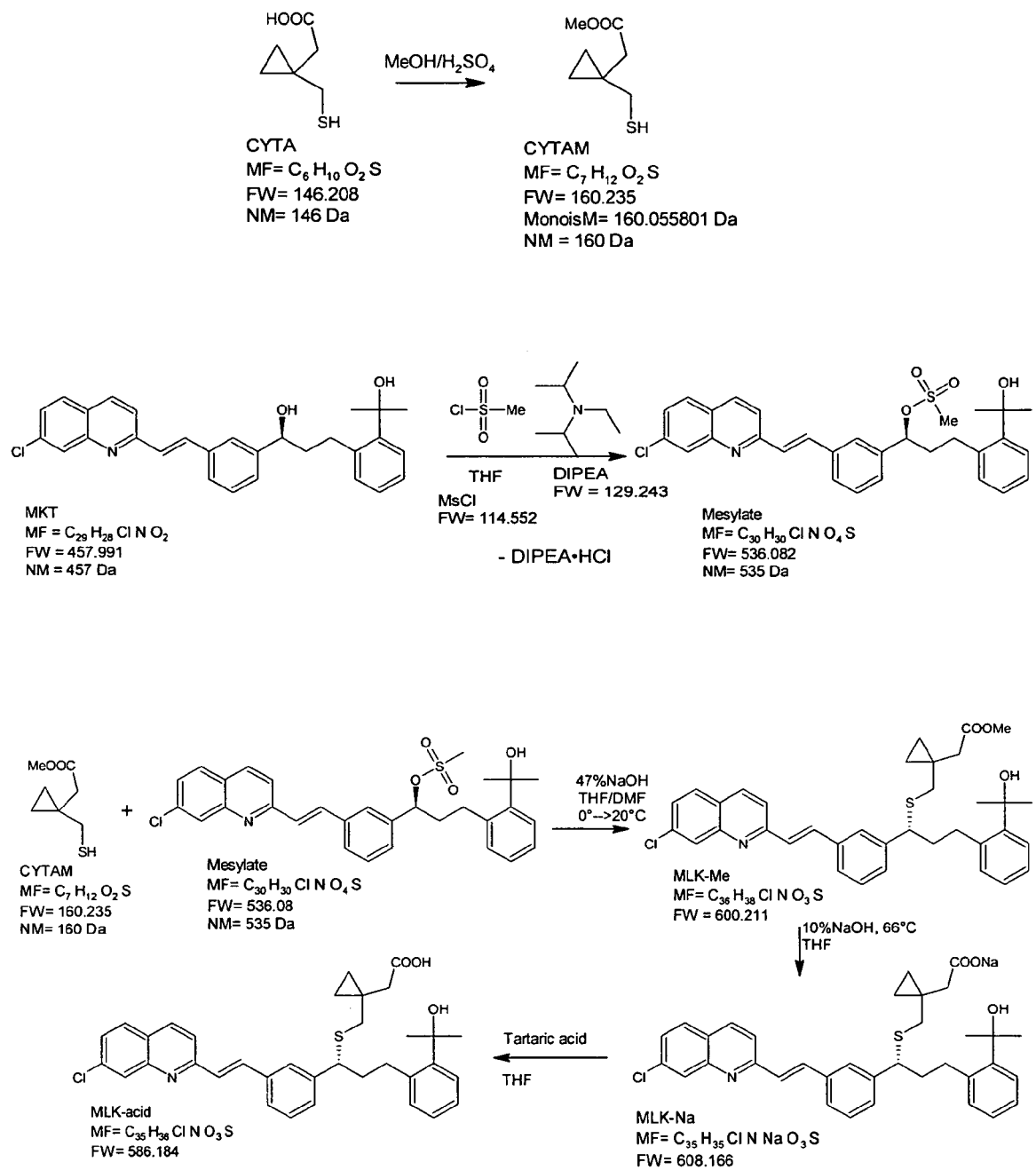
FIG. 1 depicts a process for preparing montelukast according to the present invention.

In one embodiment, the present invention provides a process for preparing a pharmaceutically acceptable salt of montelukast comprising the following steps:
 a) activating the 2-(2-(3(S)-(3-(7-chloro-2-quinolinyl)-ethenyl)phenyl)-3-((α-hydroxy)propyl)phenyl-2-propanol with a benzylsulfonyl or mesyl group;
 b) reacting the product of step a with 1-(mercaptomethyl) cyclopropaneacetic acid alkyl ester in a solvent and in the presence of a cosolvent and a base; and
 c) hydrolyzing the product of step b to obtain a pharmaceutically acceptable salt of montelukast.

In a preferred embodiment, the cosolvent is removed prior to step c. Preferably, the cosolvent is removed by evaporation or extraction.

In one embodiment, the cosolvent is an aprotic polar solvent. Preferably, the cosolvent is dimethylformamide, dimethylacetamide, or N-methyl pyrolidone. Most preferably, the cosolvent is dimethylformamide.

In another embodiment, the solvent is a weakly polar solvent or a nonpolar solvent. Preferably, the solvent is selected from the group consisting of toluene, tetrahydrofuran (THF), and dimethyl carbonate. Most preferably, the solvent is tetrahydrofuran.

In another embodiment, the base is a strong base. Most preferably, the base is selected from the group consisting of LiOH, NaOH, NaH, $NaOCH_3$, BuLi, $LiOCH_3$, $LiNPr_2$, KOtBu, and quaternary ammonium bases. In one embodiment, the base is NaOH.

In a preferred embodiment, subsequent to step c, an acid is added to obtain montelukast acid. Preferably, the acid is an organic acid or an inorganic acid. More preferably, the acid is selected from the group consisting of tartaric acid, acetic acid, sulfuric acid, hydrochloric acid, and formic acid. In one embodiment, the acid is tartaric acid.

In another embodiment, the process further comprises converting the montelukast acid to montelukast sodium by slurrying in a liquid in the presence of a sodium base. Preferably, the liquid is selected from the group consisting of MeOH, EtOH, BuOH, acetone, MIBK, isobutylacetate, heptane, isopropylether, toluene, ACN, dimethyl carbonate (DMC), and mixtures thereof. Most preferably, the liquid is DMC. Preferably, the sodium base is NaOH, sodium metoxide, or sodium tert-butoxide.

In another embodiment, the process further comprises crystallizing the montelukast acid from a crystallization solvent. Preferably the crystallization solvent is selected from a group consisting of MeOAc, EtOAc, BuOAc, ACN, ACN:acetone, EtOH, EtOH:ACN, 2-BuOH, t-BuOH, amyl alcohol, diethylcarbonate (DEC), MEK, MIBK, acetone, dibutylether, MTBE, and toluene.

In one embodiment, the process comprises steps a and b to obtain an ester of montelukast.

DETAILED DESCRIPTION OF THE INVENTION

In one embodiment, the present invention provides a process for preparing a pharmaceutically acceptable salt of montelukast. The process comprises the steps of: a) activating the 2-(2-(3(S)-(3-(7-chloro-2-quinolinyl)-ethenyl)phenyl)-3-((α-hydroxy)propyl)phenyl-2-propanol with a benzylsulfonyl or mesyl group; b) reacting the product of step a with 1-(mercaptomethyl)cyclopropaneacetic acid alkyl ester in a solvent and in the presence of a cosolvent and a base; and c) hydrolyzing the product of step b to obtain a pharmaceutically acceptable salt of montelukast. A preferred pharmaceutitically acceptable salt of montelukast is montelukast sodium. This method allows the use of a variety of bases, and it preserves the chirality of the product.

Step a, the sulfonation reaction, is preferably performed using, for example, mesylate or benzylsulfonate. Either of these preferred reagents preserves the chirality of the product.

Step b, the thiolation reaction, is carried out in a solvent. The solvent can be the same as or different from the solvent used for the sulfonation reaction in step a. In a preferred embodiment, the solvent for the thiolation reaction is a weakly polar solvent or a nonpolar solvent. Solvents that can be used for both the sulfonation and thiolation reactions include, but are not limited to, toluene (polarity index 2.4), tetrahydrofuran (THF) (polarity index 4.0), and dimethyl carbonate (DMC). THF is the most preferable solvent for the thiolation reaction.

The thiolation reaction is carried out in the presence of a cosolvent. The cosolvent is preferably an aprotic polar solvent, such as dimethylformamide (DMF), dimethylacetamide, and N-methyl pyrolidone, most preferably, DMF. In the presence of a cosolvent, the above mentioned starting material can be converted almost entirely into an ester of montelukast. Also, the instant method preserves the chirality of the product to an improved degree.

In one embodiment, the cosolvent is removed before step c. The cosolvent can be removed by any means known to one skilled in the art, for example, evaporation or extraction.

By performing the thiolation reaction with the ester of the 1-(mercaptomethyl)cyclopropaneacetic acid, a base can be used to prepare the alkylester of montelukast and subsequently, montelukast itself. Stronger bases including, but not limited to LiOH, NaOH, NaH, NaOCH$_3$, BuLi, LiOCH$_3$, LiNPr$_2$, KOtBu, and NBu$_4$OH are preferred, but weaker bases including, but not limited to Cs$_2$CO$_3$ can also be used. Preferably, the base is a reagent that is relatively inexpensive and/or relatively less dangerous. NaOH is most preferred because of its low price and selectivity.

The thiolation reaction is performed in the presence of a molar excess of base. Preferably, the amount of base is about 1.2 to about 7.5 mole per mole of substrate (mesylate), more preferably about 2.4 to about 2.6 mole per mole substrate.

The reaction temperature is preferably about −10° C. to about 30° C., and most preferably about 5° C. At the end of the reaction, the temperature rises to about room temperature.

In one embodiment, the process comprises steps a and b to obtain an ester of montelukast.

The hydrolysis of the alkylester of montelukast to montelukast acid and the subsequent formation of montelukast sodium salt can be performed by any method known to one of skill in the art. See, for example, U.S. Pat. No. 5,614,632. In one embodiment, the montelukast acid is converted to montelukast sodium by slurrying in a liquid and in the presence of a sodium base. The liquid is preferably MeOH, EtOH, BuOH, acetone, MIBK, isobutylacetate, heptane, isopropylether, toluene, ACN, dimethyl carbonate (DMC), or mixtures thereof, and most preferably DMC. The sodium base is preferably NaOH, sodium metoxide, or sodium tert-butoxide (t-BuONa).

The methods of the present invention may comprise preparing montelukast acid. Preparing montelukast acid may comprise adding an acid after the hydrolyzing step. The acid can be an organic acid or an inorganic acid. The acid is preferably acetic acid, sulfuric acid, hydrochloric acid, or formic acid. Most preferably, the acid is tartaric acid.

The method may further comprise crystallizing the montelukast acid from a crystallization solvent. The crystallization solvent can be, for example, MeOAc, EtOAc, BuOAc, ACN, ACN:acetone, EtOH, EtOH:ACN, 2-BuOH, t-BuOH, amyl alcohol, diethylcarbonate (DEC), MEK, MIBK, acetone, dibutylether, MTBE, or toluene.

Preparing montelukast sodium from montelukast acid can be performed by any method known to one of skill in the art. In one embodiment, this preparation is performed using dimethylcarbonate (DMC) and either NaOH, sodium metoxide, or sodium tert-butoxide (t-BuONa).

Montelukast prepared by an embodiment of the present invention may be used for pharmaceutical formulations and for use in treating respiratory diseases. A pharmaceutical formulation may be prepared by combining the montelukast prepared by an embodiment of the present invention with one or more pharmaceutical excipients.

Having described the invention, the invention is further illustrated by the following non-limiting examples.

EXAMPLES

Example 1

Preparation of 1-(mercaptomethyl)cyclopropaneacetic acid methyl ester

To a 3 L flask, a solution of 1-(mercaptomethyl)cyclopropaneacetic acid (330.7 g) in methanol (1500 ml) was charged. 96% sulfuric acid (36 g) was added, and the reaction mixture was stirred for 5 h at 19-22° C. The reaction mixture was concentrated to ¼ of its volume at 50° C. under reduced pressure, and the residue was partitioned between water (1000 ml) and ethyl acetate (500 ml). The organic phase was separated, washed with 10% NaHCO$_3$ and 5% NaCl (200 ml), and dried overnight over anhydrous sodium sulfate. The mixture was filtered and evaporated at 50° C. under reduced pressure, to afford 315.7 g of the crude 1-(mercaptomethyl)cyclopropaneacetic acid methyl ester, as a colored liquid with a strong, unpleasant odor.

A part of the product (84.48 g) was distilled under reduced pressure to afford 66 g of the product in a purity of 95%. B.P. 75-76° C./5 mbar Example 2

Preparation of 1-(mercaptomethyl)cyclopropaneacetic acid ethyl ester

To a 3 L flask, a solution of 1-(mercaptomethyl)cyclopropaneacetic acid (204.5 g) in ethanol (1000 ml) was charged. 96% sulfuric acid (22.73 g) was added, and the reaction mixture was stirred for 3 h at 19-22° C. The reaction mixture was concentrated to ¼ of its volume at 50° C. under reduced pressure, and the residue was partitioned between water (1000 ml) and ethyl acetate (200 ml). The organic phase was separated, washed with 10% NaHCO$_3$ (400 ml), and dried for 2 h over anhydrous sodium sulfate. The mixture was filtered and evaporated at 50° C., under reduced pressure, to afford 197.9 g of the crude 1-(mercaptomethyl)cyclopropaneacetic acid ethyl ester, as a slightly colored liquid with a strong, unpleasant odor.

A part of the product (71.6 g) was distilled under reduced pressure to afford 49.5 g of the product in a purity of 90%, B.P. 57-58° C./0.7 mbar.

Example 3

Preparation of [R-(E)]-1-[[[3-[2-(7-chloro-2-quinolinyl)ethenyl]phenyl]-3-[2-(1-hydroxy-1-methylethyl) phenyl]propyl]thio]methyl]cyclopropaneacetic acid methyl ester using a 47% sodium hydroxide solution To a 0.1 L flask, a solution of 1-(mercaptomethyl)cyclopropaneacetic acid methyl ester (2.92 g) in DMF (25 ml) was charged. 47% NaOH solution (1.56 g) was added, under an inert atmosphere. The mixture was stirred for 5 min, and 22 ml of a cold solution of about 25% content of 2-(2-(3(S)-(3-(7-chloro-2-quinolinyl)-ethenyl)phenyl)-3-((α-phenyl-methanesulfonyloxy) propyl)phenyl-2-propanol dissolved in THF was added over 4 min to afford a viscous solution. The reaction mixture was stirred overnight at about 20° C., and partitioned between a 5% NaCl solution (100 ml) and ethyl acetate (50 ml). The organic extract was separated, washed with water (2×50 ml) and brine, dried with anhydrous sodium sulfate, and evaporated under reduced pressure at 50° C., to afford 8.78 g of the reaction product, containing 77% [R-(E)]-1-[[[3-[2-(7-chloro-2-quinolinyl)ethenyl]phenyl]-3-[2-(1-hydroxy-1-methylethyl)phenyl]propyl]thio]methyl]cyclopropaneacetic acid methyl ester. Yield 84%.

In the same manner, reactions were carried out using the following co-solvents: acetonitrile, N-methylpyrrolidone and N,N-dimethylacetamide. The results are summarized in Table 1.

TABLE 1

| Example | Solvent | Yield, % |
|---|---|---|
| Example 4 | Dimethylacetamide | 81 |
| Example 5 | N-methyl-pyrolidone | 37 |

Example 6

Preparation of 2-(2-(3(S)-(3-(7-chloro-2-quinolinyl)-ethenyl)phenyl)-3-methanesulfonyloxypropyl)phenyl-2-propanol To a solution of 2-(2-(3(S)-(3-(7-chloro-2-quinolinyl)-ethenyl)phenyl)-3-hydroxypropyl)phenyl-2-propanol (10.04 g) in anhydrous THF (40 ml), cooled to −10° C.±3° C., was gradually added diisopropylethylamine (5.2 ml), keeping the temperature at −5° C.±2° C. Methanesulfonyl chloride (2.79 g) was added in portions over 3 min, maintaining the temperature at −5° C.±3° C., under an inert atmosphere. (The reaction is strongly exothermic.) The reaction mixture was stirred for 0.5 h at −5° C.±2° C. and filtered under an inert atmosphere. The cake was washed with cooled THF (8 ml), and the cold combined filtrate was used immediately in the thiolation step.

Example 7

Preparation of 2-(2-(3(S)-(3-(7-chloro-2-quinolinyl)-ethenyl)phenyl)-3-((α-phenylmethanesulfonyloxy) propyl)phenyl-2-propanol To a solution of 2-(2-(3(S)-(3-(7-chloro-2-quinolinyl)ethenyl)phenyl)-3-hydroxypropyl)phenyl-2-propanol (9.99 g) in anhydrous THF (30 ml) cooled to −10° C.±3° C., was added diisopropylethylamine (5.9 ml) gradually, keeping the temperature at −7° C.±2° C. A solution of α-toluenesulfonylchloride (4.87 g) in THF (15 ml) was added in portions over 13 min, maintaining the temperature at −5° C.±3° C., under an inert atmosphere (The reaction is strongly exothermic.) The reaction mixture was stirred for 2 h at −8° C.±2° C. and filtered under an inert atmosphere. The cake was washed with cooled THF (8 ml) and the cold combined filtrate was used immediately in the thiolation step.

Example 8

Preparation of [R-(E)]-1-[[[3-[2-(7-chloro-2-quinolinyl)ethenyl]phenyl]-3-[2-(1-hydroxy-1-methylethyl) phenyl]propyl]thio]methyl]cyclopropaneacetic acid sodium salt

[R-(E)]-1-[[[3-[2-(7-chloro-2-quinolinyl)ethenyl]phenyl]-3-[2-(1-hydroxy-1-methylethyl)phenyl]propyl]thio] methyl]cyclopropaneacetic acid methyl ester from Example 3 (about 8.7 g) was diluted with methanol (23 ml). A 10% NaOH solution (7.7 g) was added, and the turbid solution was clarified with THF (1 ml). The clear solution was stirred for 50 h at room temperature and evaporated. The oily residue was partitioned between water (50 ml) and ethyl acetate (60 ml). The organic phase was washed with 5% NaCl (20 ml) to remove excess NaOH and diluted with heptane (30 ml), to afford the separation of a heavy liquid. The lower phase was separated, stripped with ethanol and evaporated to dryness at 50° C., to afford 3.19 g of the crude product, montelukast sodium, purity 91%. Yield 50%.

Example 9

Preparation of [R-(E)]-1-[[[3-[2-(7-chloro-2-quinolinyl)ethenyl]phenyl]-3-[2-(1-hydroxy-1-methylethyl) phenyl]propyl]thio]methyl]cyclopropaneacetic acid To a solution of 1-(mercaptomethyl)cyclopropaneacetic acid methyl ester (4.43 g) in DMF (17 ml) cooled to −12° C., was added a 47% NaOH solution (2.01 g) under an inert atmosphere, in darkness. The mixture was stirred for 10 min at −10° C. and a cold solution of 2-(2-(3(S)-(3-(7-chloro-2-quinolinyl)-ethenyl)phenyl)-3-methanesulfonyl oxypropyl) phenyl-2-propanol (about −20° C., 38 ml) was added over 2 min, to afford a viscous solution. The reaction mixture was stirred for 3 h at −10° C. and evaporated at 42° C.-45° C. to remove most of the volatiles. The residue was partitioned between 5% NaCl (50 ml) and THF (25 ml). The aqueous phase was separated, extracted with THF (20 ml) and discarded. The organic extract was combined with the organic phase, washed with 5% NaCl (25 ml), and mixed with a 10% NaOH solution (41.79 g). The mixture was heated overnight at 50° C., under stirring, in darkness. The aqueous phase was separated. The organic phase was washed with 5% NaCl (50 ml) to remove excess NaOH and acidified with a 0.5 M tartaric acid solution in 50% aqueous THF, to adjust the pH to 4-5. The lower aqueous phase was separated and discarded. The organic solution was evaporated to dryness to give 10.2 g of the crude product as a slightly colored solid. Purity 81%. Yield 74%.

Example 10

Preparation of [R-(E)]-1-[[[3-[2-(7-chloro-2-quinolinyl)ethenyl]phenyl]-3-[2-(1-hydroxy-1-methylethyl)phenyl]propyl]thio]methyl]cyclopropaneacetic acid methyl ester using NaH Sodium hydride (0.79 g) was placed into the reaction flask, flushed with anhydrous THF (20 ml), and suspended in THF (10 ml). A solution of 1-(mercaptomethyl) cyclopropaneacetic acid methyl ester (2.93 g) in THF (5 ml) was added all at once, and the reaction mixture was stirred for 1 h at ambient temperature until the cessation of gas evolution. N,N-Dimethylformamide (25 ml) was added, followed by the cold solution of 2-(2-(3(S)-(3-(7-chloro-2-quinolinyl)-ethenyl)phenyl)-3-methanesulfonyl oxypropyl)phenyl-2-propanol (about −5° C., 20 ml), about 25% in solution of THF. The reaction mixture was stirred for 4 h at room temperature and partitioned between ethyl acetate (50 ml) and 5% NaCl (100 ml). The upper, organic layer was separated, washed with water (2×25 ml) and brine, dried with anhydrous sodium sulfate for 3 h, and evaporated under reduced pressure at 50° C., to afford 8.44 g of the reaction product containing 66% of the desired molecule. Yield 69%.

In the same manner, reactions were carried out using the other bases. The results are summarized in Table 2.

TABLE 2

| Example | Base | Yield, % |
|---|---|---|
| Example 11 | Di-isopropyl NLi | 46 |
| Example 12 | Sodium metoxide | 76 |
| Example 13 | K₂CO₃ | 55 |
| Example 14 | tetrabutylammonium hydroxide | 61 |

Example 15

Preparation of [R-(E)]-1-[[[3-[2-(7-chloro-2-quinolinyl)ethenyl]phenyl]-3-[2-(1-hydroxy-1-methylethyl)phenyl]propyl]thio]methyl]cyclopropaneacetic acid

[R-(E)]-1-[[[3-[2-(7-chloro-2-quinolinyl)ethenyl]phenyl]-3-[2-(1-hydroxy-1-methylethyl)phenyl]propyl]thio]methyl]cyclopropaneacetic acid methyl ester from Example 3 (51.3 g, content 42%) was dissolved with THF (103 ml). A 10% NaOH solution (103 g) was added, and the turbid solution was clarified with methanol (50 ml). The clear solution was stirred for 5 h at room temperature and diluted with toluene (150 ml) to induce the phase separation. The organic phase was separated and treated with 0.5 M tartaric acid (103 g) to adjust to pH 4. The upper organic phase was separated, concentrated to volume 100 ml to strip water off, and filtered. The filtrate was allowed to cool to room temperature, under stirring, to afford the precipitation. The cake was filtered, washed with toluene and dried at 48-50° C. under reduced pressure to yield 15.4 g of the crystalline product, montelukast acid, purity 94%. Yield 64%. Repeated crystallization from toluene afforded the product with purity of 97%.

Example 16

Purification of [R-(E)]-1-[[[3-[2-(7-chloro-2-quinolinyl)ethenyl]phenyl]-3-[2-(1-hydroxy-1-methylethyl)phenyl]propyl]thio]methyl]cyclopropaneacetic acid sodium salt To a 150 mL reactor, equipped with a mechanical stirrer, montelukast acid (5 g), dimethylcarbonate (DMC) (25 mL), and NaOH (0.36 g) were added at ambient temperature. The reaction was stirred and then heated to 35° C. for 9 hours. The reaction mixture was then cooled to 25° C. over 0.5 hour and stirred overnight at 25° C. DMC (10 ml) was added, and the reaction mixture was stirred for an additional 15 min. The solid was then filtered under reduced pressure and under nitrogen. The cake was washed with DMC (10 mL). The solid was dried in a vacuum oven overnight at 50° C. to obtain a white powder (81.5%).

Example 17

Purification of [R-(E)]-1-[[[3-[2-(7-chloro-2-quinolinyl)ethenyl]phenyl]-3-[2-(1-hydroxy-1-methylethyl)phenyl]propyl]thio]methyl]cyclopropaneacetic acid sodium salt To a 150 ml reactor, montelukast acid (7 g), t-BuONa (1.2 g), and then DMC (35 mL) were added. The reaction was stirred at 25° C. for 7 h. When the mixture became much thicker, DMC (35 mL) was added. The mixture was then stirred for 10 min, and the solid was filtered under reduced pressure and under nitrogen. The cake was washed with DMC (14 mL). The solid was dried in vacuum oven at 50° C. overnight to get a white solid.

Example 18

Crystallization of Montelukast (MLK) free acid

The general procedure for montelukast acid crystallization is described below. The specific reaction conditions are shown in Table 3.

To a 100 mL flask equipped with a magnetic stirrer and a reflux condenser, montelukast free acid (1.5 g) and crystallization solvent (3.75 mL) were added. The mixture was heated and crystallization solvent was added to obtain a clear solution. After obtaining a clear solution, the mixture was cooled slowly to the indicated temperature.

TABLE 3

Crystallization of Montelukast free acid

| Solvent | Total Volume (mL/g MLK) | Heating Temp | Cooling Temp | Yield (%) |
|---|---|---|---|---|
| MeOAc | 8 | Reflux | RT | 60 |
| MeOAc | 8 | Reflux | 5° C. | 74 |
| EtOAc | 5.33 | Reflux | RT | 76 |
| BuOAc | 3.66 | Reflux | RT | 80 |
| ACN | 20 | Reflux | RT | 80 |
| ACN | 94 | 60° C. | RT | 80 |
| ACN | 20 | Reflux | RT | 86 |
| ACN:Acetone 7:8 | 10 | 60° C. | RT | 52.6 |
| EtOH | 4 | Reflux | RT | 74 |
| EtOH | 4 | Reflux | 5° C. | 82 |
| EtOH:ACN 1.3:10 | 7.5 | Reflux | RT | 80 |
| 2-BuOH | 2.66 | Reflux | RT | 80 |
| t-BuOH | 5.33 | Reflux | RT | 84 |
| Amyl-OH | 2.66 | Reflux | RT | 76.6 |
| DEC | 2.66 | 110° C. | RT | 77 |
| MEK | 2.66 | Reflux | RT | 32 |
| MEK | 4 | 60° C. | RT | 43 |
| Acetone then Water 2.6:1 | 6 | Reflux | 5° C. | 80 |
| MIBK | 2.6 | 96° C. | RT | 52 |
| DiBu-ether | 40 | 110° C. | RT | 84 |
| MTBE | 50 | Reflux | RT | 33 |
| Toluene | 6.66 | Reflux | RT | 72 |

Having thus described the invention with reference to particular preferred embodiments and illustrative examples, those in the art may appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. All references mentioned herein are incorporated in their entirety.

What is claimed is:

1. A process for preparing an ester of montelukast comprising the following steps:
   a) activating 2-(2-(3(S)-(3-(7-chloro-2-quinolinyl)-ethenyl)phenyl)-3-(($\alpha$-hydroxy)propyl)phenyl-2-propanol with a benzylsulfonyl or mesyl group; and
   b) reacting the product of step (a) with 1-(mercaptomethyl)cyclopropaneacetic acid alkyl ester in a solvent and in the presence of a cosolvent and a base to obtain an ester of montelukast.

2. The process of claim 1 further comprising hydrolyzing the product of step (b) to obtain a pharmaceutically acceptable salt of montelukast.

3. The process of claim 2, wherein prior to hydrolyzing the product of step (b), the cosolvent is removed.

4. The process of claim 3, wherein the cosolvent is removed by evaporation or extraction.

5. The process of claim 1, wherein the cosolvent is an aprotic polar solvent.

6. The process of claim 5, wherein the cosolvent is dimethylformamide, dimethylacetamide, or N-methyl pyrrolidone.

7. The process of claim 6, wherein the cosolvent is dimethylformamide.

8. The process of claim 1, wherein the solvent is a weakly polar solvent or a nonpolar solvent.

9. The process of claim 8, wherein said solvent is selected from the group consisting of toluene, tetrahydrofuran, and dimethyl carbonate.

10. The process of claim 9, wherein the solvent is tetrahydrofuran.

11. The process of claim 1, wherein the base is a strong base.

12. The process of claim 11, wherein the base is selected from the group consisting of LiOH, NaOH, NaH, NaOCH$_3$, BuLi, LiOCH$_3$, LiNPr$_2$, KOtBu, and quaternary ammonium bases.

13. The process of claim 12 wherein the base is NaOH.

14. The process of claim 2, wherein subsequent to hydrolysis, an acid is added to the pharmaceutically acceptable to obtain montelukast acid.

15. The process of claim 14, wherein the acid is an organic acid or an inorganic acid.

16. The process of claim 15, wherein the acid is selected from the group consisting of tartaric acid, acetic acid, sulfuric acid, hydrochloric acid, and formic acid.

17. The process of claim 16, wherein the acid is a tartaric acid.

18. The process of claim 14, further comprising converting the montelukast acid to montelukast sodium by slurrying in a liquid in the presence of a sodium base.

19. The process of claim 18, wherein the liquid is selected from the group consisting of MeOH, EtOH, BuOH, acetone, MIBK, isobutylacetate, heptane, isopropylether, toluene, ACN, dimethyl carbonate, and mixtures thereof.

20. The process of claim 19, wherein the liquid is dimethyl carbonate.

21. The process of claim 18, wherein the sodium base is NaOH, sodium methoxide, or sodium tert-butoxide.

22. The process of claim 14, further comprising crystallizing the montelukast acid from a crystallization solvent.

23. The process of claim 22, wherein the crystallization solvent is selected from the group consisting of MeOAc, EtOAc, BuOAc, ACN, ACN:acetone, EtOH, EtOH:ACN, 2-BuOH, t-BuOH, amyl alcohol, diethylcarbonate, MEK, MIBK, acetone, dibutylether, MTBE, and toluene.

24. The process of claim 22, further comprising converting the montelukast acid to montelukast sodium by slurrying in a liquid in the presence of sodium base.

25. The process of claim 24, wherein the liquid is selected from the group consisting of MeOH, EtOH, BuOH, acetone, MIBK, isobutylacetate, heptane, isopropylether, toluene, ACN, dimethyl carbonate, and mixtures thereof.

26. The process of claim 25, wherein the liquid is dimethyl carbonate.

27. The process of claim 24, wherein the sodium base is NaOH, sodium methoxide, or sodium tert-butoxide.

* * * * *